US009617300B2

(12) United States Patent
Yamada et al.

(10) Patent No.: US 9,617,300 B2
(45) Date of Patent: Apr. 11, 2017

(54) DIPEPTIDYL PEPTIDASE-IV INHIBITOR

(71) Applicant: MORINAGA MILK INDUSTRY CO., LTD, Tokyo (JP)

(72) Inventors: Akio Yamada, Kanagawa (JP); Takuma Sakurai, Kanagawa (JP); Daisuke Ochi, Kanagawa (JP)

(73) Assignee: MORINAGA MILK INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 14/383,618

(22) PCT Filed: Feb. 21, 2013

(86) PCT No.: PCT/JP2013/054291
§ 371 (c)(1),
(2) Date: Sep. 8, 2014

(87) PCT Pub. No.: WO2013/133031
PCT Pub. Date: Sep. 12, 2013

(65) Prior Publication Data
US 2015/0232510 A1    Aug. 20, 2015

(30) Foreign Application Priority Data

Mar. 9, 2012    (JP) .................................. 2012-053855

(51) Int. Cl.
*C07K 5/083* (2006.01)
*A61K 38/00* (2006.01)

(52) U.S. Cl.
CPC ............ *C07K 5/0808* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,994,987 B1 | 2/2006 | Yamamoto et al. | 435/68.1 |
| 2003/0130199 A1* | 7/2003 | von Hoersten | A61K 31/401 514/19.3 |
| 2003/0176357 A1 | 9/2003 | Pospisilik et al. | |
| 2005/0004041 A1 | 1/2005 | Tamura et al. | 514/18 |
| 2009/0075904 A1 | 3/2009 | Boots | 514/16 |
| 2012/0157395 A1 | 6/2012 | Ibuki et al. | 514/21.9 |

FOREIGN PATENT DOCUMENTS

| | | | |
|---|---|---|---|
| CN | 1660888 A * | 8/2005 | |
| EP | 0 801 073 A2 | 10/1997 | |
| JP | 6-40944 A | 2/1994 | |
| JP | 7-101982 A | 4/1995 | |
| JP | 8-99994 A | 4/1996 | |
| JP | 9-227591 A | 9/1997 | |
| JP | 2001-136995 A | 5/2001 | |
| JP | 2003-104997 A | 4/2003 | |
| JP | 2007-39424 A | 2/2007 |
| JP | 2008-527011 A | 7/2008 |
| JP | 2008-280291 A | 11/2008 |
| JP | 2011-144167 A | 7/2011 |
| WO | WO 99/48910 A1 | 9/1999 |
| WO | WO 03/031574 A2 | 4/2003 |
| WO | WO 03/031623 A1 | 4/2003 |
| WO | WO 03/044044 A1 | 5/2003 |
| WO | WO 2006/068480 A2 | 6/2006 |
| WO | WO 2006/078676 A2 | 7/2006 |
| WO | WO 2006/108211 A1 | 10/2006 |
| WO | WO 2009/052489 A2 | 4/2009 |
| WO | WO 2010/072327 A2 | 7/2010 |
| WO | WO 2010/077988 A2 | 7/2010 |
| WO | WO 2011/007612 A1 | 1/2011 |

OTHER PUBLICATIONS

Platerink et al. Anal Bioanal Chem. 391:299-307;2008.*
Kevin Ryan et al., Construction of Science-Selective Peptide Receptors From Conformationally Restricted *ETA*- and *THETA*- Amino Acids, Aug. 10, 1999, pp. 2673-2678.
Chris J. van Platerink et al., Application of at-line two-dimensional liquid chromatography-mass spectrometry for identification of small hydrophilic angiotensin I-inhibiting peptides in milk hydrolysates, Apr. 9, 2008, pp. 299-307.
Meimei Yin et al., Early and late effects of the dPP-4 inhibitor vildagliptin in a rat model of post-myocardial infarction heart failure, 2011, pp. 1-10.
Pleun C.M. van Poppel et al., Vildagliptin Improves Endothelium-dependent Vasodilation in Type 2 Diabetes, Sep. 2011, pp. 2072-2077.
Sachiko Hattori, Sitagliptin reduces albuminuria in patients with type 2 diabetes, Dec. 20, 2010, pp. 69-73.
Juichi Matsubara, et al., A Dipeptidyl Peptidase-4 Inhibitor, Des-Fluoro-Sitagliptin, Improves Endothelial Function and Reduces Atherosclerotic Lesion Formation in Apolipoprotein E-Deficient Mice, 2012, pp. 265-276.
F. Minervini et al., Angiotensin I-Converting-Enzyme-Inhibitory and Antibacterial Peptides from *Lactobacillus helveticus* PR4 Proteinase-Hydrolyzed Caseins of Milk from Sic Species, 2003, pp. 5297-5305.

(Continued)

*Primary Examiner* — Amber D Steele
*Assistant Examiner* — Schuyler Milton
(74) *Attorney, Agent, or Firm* — Birch, Stewart, Kolach & Birch, LLP

(57) ABSTRACT

An excellent peptidyl peptidase-IV inhibitor and the like are provided. A peptide consisting of Val-Pro-X wherein X represents an amino acid residue (except for L-proline residue); the aforementioned X is preferably one selected from a basic amino acid residue, an aliphatic neutral amino acid residue, an amide group-carrying neutral amino acid residue, or an aromatic group-carrying neutral amino acid residue; the aforementioned X is preferably one selected from an alanine residue, a glutamine residue, a methionine residue, an asparagine residue, a glycine residue, a valine residue, a tyrosine residue, a serine residue, and a lysine residue; a dipeptidyl peptidase-IV inhibitor, a blood sugar rise suppressing agent, a vascular endothelial disorder suppressing agent, and an angiotensin converting enzyme inhibitor containing the aforementioned peptide as an active ingredient.

9 Claims, 2 Drawing Sheets

(56) References Cited

OTHER PUBLICATIONS

International Search Report mailed May 23, 2013, issued to corresponding International Patent Application No. PCT/JP2013/054291.
Endroczi et al., "Dipeptidyl Peptidase IV (DP IV) and Superoxide Dismutase Activity in Thymus-Derived Lymphocytes: Effects of Inhibitory Peptides and $Zn^{2+}$ In Vitro", Acia Physiologica Hungarica, vol. 75, No. 1, pp. 35-44, 1990.
English translation of Japanese Office Action dated Jun. 2, 2015, for Japanese Application No. 2014-503756.
Extended European Search Report dated Dec. 1, 2015, for European Application No. 13758259.9.

* cited by examiner

ID NO:1) (hereinafter referred to also as "peptide VPX")
DIPEPTIDYL PEPTIDASE-IV INHIBITOR

CROSS-REFERENCE TO RELATED APPLICATIONS

This application is a national stage of International Application No. PCT/JP2013/054291, filed Feb. 21, 2013, which claims the benefit of Japanese Application No. 2012-053855, filed Mar. 9, 2012, in the Japanese Patent Office. All disclosures of the document(s) named above are incorporated herein by reference.

BACKGROUND OF THE INVENTION

1. Field of the Invention

The present invention relates to a dipeptidyl peptidase-IV inhibitor and the like.

2. Description of the Related Art

Dipeptidyl peptidase-IV (hereinafter referred to also as "DPP-4") is a multifunctional transmembrane glycoprotein having an N-terminal dipeptidase activity. It is present on the cells of most mammalian animals, and its presence in various tissues such as liver, kidney, small intestine, salivary gland, blood cells, plasma, and the like raises an assumption that it plays a broad range of in vivo roles, which makes it an enzyme which is attractive as a drug discovery target in these days.

The dipeptidyl peptidase-IV is known as a lytic enzyme to incretin's glucagon-like peptide-1 (hereinafter referred to as "GLP-1") and glucose-dependent insulinotropic polypeptide (hereinafter referred to as "GIP"). This GLP-1 is released after meal, and has a diverse effect including insulin biosynthesis- and secretion-responsive glucose inducible stimulation, glucagon secretion suppression, gene expression regulation, B-cell trophic effect, food intake suppression, and gastric content output slowing. In addition, dipeptidyl peptidase-IV inhibition serves to suppress degradation of incretin's GLP-1 and GIP, whose concentrations in blood are then elevated. As a result, the insulin secretion is promoted and the blood sugar level is reduced, as is known. This incretin-driven insulin secretion promotion requires a hyperglycemic level as an operating condition. Accordingly, the dipeptidyl peptidase-IV inhibition in a diabetes case caused by a reduction in insulin secretion among type II diabetes is at a lower risk of a side effect such as hypoglycemia which is caused by conventional insulin secretion promotors.

As discussed above, the dipeptidyl peptidase-IV inhibitor having a dipeptidyl peptidase-IV activity inhibiting effect is to be utilized as an anti-diabetic agent. Nevertheless, the dipeptidyl peptidase-IV inhibitor is regarded still as a new type therapeutic agent when compared with the insulin secretion suppressing agents and the glucose absorption inhibiting agents. In addition, the first step of the diabetic therapy involves dietetic treatment and kinesitherapy, whose inability, in some cases, of controlling the blood sugar level leads, to use of pharmaceuticals for treating diabetes. As a result, it can be considered that a substance having a dipeptidyl peptidase-IV inhibiting activity can be provided as a supplement or a food additive contributes greatly to the improvement of the blood sugar level.

Patent Document 1 discloses that a dicyclic pyrimidine can be used as a dipeptidyl peptidase-IV inhibitor for the therapy or the prophylaxis of diabetes.

Patent Document 2 discloses that a casein was subjected to an alkaline degradation while controlling pH and temperature followed by an enzymatic hydrolysis using a preparation of various enzymes such as a protease to obtain a hydrolysate which was then separated and purified into various peptides, from which one having a dipeptidyl peptidase-IV inhibiting effect was further identified. Otherwise, there are disclosures relating to food-derived dipeptidyl peptidase-IV inhibiting substances (for example, see Patent Documents 3 to 5).

Table 2 of Patent Document 6 indicates isolated peptides each of which was separated as a single peptide from a casein or whey hydrolysate, namely, IPI, LPL, KVLP, LPVPQK, VPLGTQ, VPYPQ, PLLQ, GPFP, LPVPQ, LPQYL, MPLW, YVPEPF, PQSVLS, PFP, LPVP, EMPFPK, LPLP, GPFPIIV, APFPE, HPIK, and APFPEVF, and the results of the dipeptidyl peptidase-IV inhibiting tests of these isolated peptides were disclosed.

CITATION LIST

Patent Literatures

[Patent Document 1] JP-T No. 2008-527011
[Patent Document 2] US-A No. 2009/0075904
[Patent Document 3] JP-A No. 2011-144167
[Patent Document 4] JP-A No. 2007-039424
[Patent Document 5] JP-A No. 2008-280291
[Patent Document 6] International publication WO 2006/068480

SUMMARY OF THE INVENTION

Technical Problem

While the dipeptidyl peptidase-IV inhibitors have been disclosed as discussed above, it is required, for example in Patent Document 1, to conduct a complicated synthetic process for an organically synthesized compound, and the safety should be subjected to a future verification. Any of the dipeptidyl peptidase-IV inhibitors involve features to be investigated, and previously there are no sufficient researches of the dipeptidyl peptidase-IV inhibiting substances.

In addition, since a peptide may have a beneficial bioactive effect, a novel peptide is searched for and various bioactive effects of the peptide are explored. Nevertheless, the peptide, when associated with increased or reduced amino acids or partially different amino acids, may have reduced or no bioactive effects, and it is difficult, even in the hydrolysates of a milk-derived protein such as a casein, to find a new or known peptide having intended bioactive effects because of the coexistence of numerous peptides.

Accordingly, the present invention is to provide excellent dipeptidyl peptidase-IV inhibitors.

Solution to Problem

As a result of intensive study to solve the aforementioned problems, it was discovered that a casein hydrolysate obtained by hydrolyzing casein by a certain enzyme contains more than one peptide having a dipeptidyl peptidase-IV inhibiting effect, including novel peptides disclosed therein. Based on these results, a peptide which is a peptide having a sequence represented by Val-Pro-X wherein X represents an amino acid residue (except for L-proline residue) (SEQ ID NO:1) (hereinafter referred to also as "peptide VPX") was discovered.

Moreover, this peptides are considered to be highly safe because they are food-derived component, and this peptide VPX can be provided as a supplement or a food additive.

Accordingly, the peptides VPX of the present disclosure are considered to be able to contribute greatly to the improvement of the blood sugar level. Also since the peptides VPX of the present disclosure include those peptides having an angiotensin converting enzyme inhibiting effect, the peptides VPX of the present disclosure are considered to be able to contribute greatly to the improvement in hypertension.

Based on the understanding described above, the peptides VPX of the present disclosure can be regarded as effective substances with increased added values.

Thus, the present invention is peptides consisting of Val-Pro-X wherein X represents an amino acid residue (except for L-proline residue).

Also it is a dipeptidyl peptidase-IV inhibitor and/or an angiotensin converting enzyme inhibitor containing a peptide consisting of Val-Pro-X wherein X represents an amino acid residue (except for L-proline residue) as an active ingredient.

Also it is a blood sugar rise suppressing agent, a hyperglycemia ameliorating agent, an anti-diabetic agent, a hypotensive agent, an anti-hypertension agent, or a vascular endothelial disorder suppressing agent containing a peptide consisting of Val-Pro-X wherein X represents an amino acid residue (except for L-proline residue) as an active ingredient.

It is preferable that the aforementioned X is a basic amino acid residue, an aliphatic neutral amino acid residue, a hydroxy group-carrying neutral amino acid residue, an amide group-carrying neutral amino acid residue, or an aromatic group-carrying neutral amino acid residue.

It is preferable that the aforementioned X is one selected from an alanine residue, a glutamine residue, a methionine residue, an asparagine residue, a glycine residue, a valine residue, a tyrosine residue, a serine residue, and a lysine residue. L-amino acids are also preferred.

Those in which the aforementioned peptide is one selected from the peptide sequences consisting of any of the following amino acid sequences (a) to (i):

(a) Val-Pro-Ala (VPA: SEQ ID NO: 2)

(b) Val-Pro-Gln (VPQ: SEQ ID NO: 3)

(c) Val-Pro-Met (VPM: SEQ ID NO: 4)

(d) Val-Pro-Asn (VPN: SEQ ID NO: 5)

(e) Val-Pro-Gly (VPG: SEQ ID NO: 6)

(f) Val-Pro-Val (VPV: SEQ ID NO: 7)

(g) Val-Pro-Tyr (VPY: SEQ ID NO: 8)

(h) Val-Pro-Ser (VPS: SEQ ID NO: 9)

(i) Val-Pro-Lys (VPK: SEQ ID NO: 10)

are preferred.

The present invention can provide a dipeptidyl peptidase-IV inhibitor, a blood sugar rise suppressing agent, a vascular endothelial disorder suppressing agent, and the like, since the peptide VPX of the present invention has an excellent dipeptidyl peptidase-IV inhibiting effect.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Figure 1:
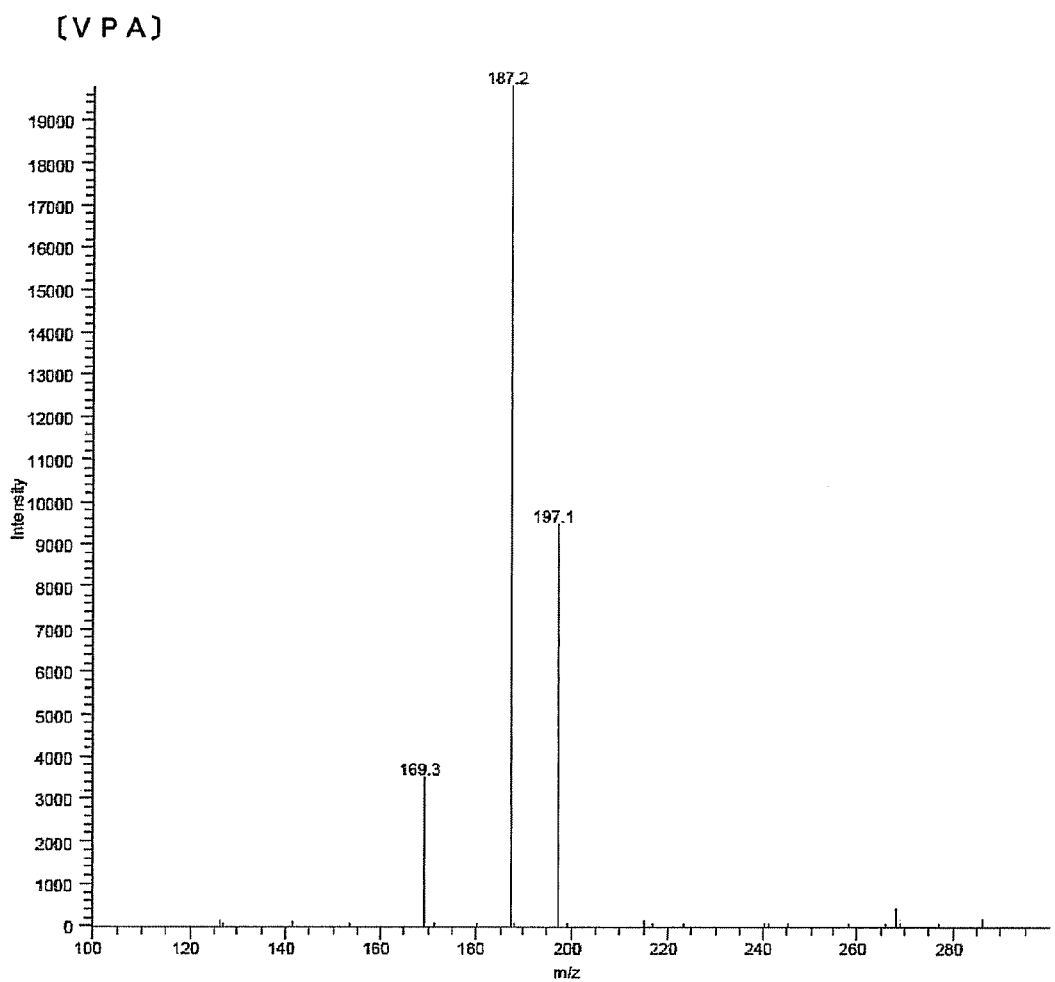
FIG. 1 is a schematic view showing the results of the MS/MS analysis of the peptide VPA of the present disclosure.

Reference will now be made in detail to the present embodiments of the present invention, examples of which are illustrated in the accompanying drawings, wherein like reference numerals refer to the like elements throughout. The embodiments are described below in order to explain the present invention by referring to the examples.

The peptide of the present disclosure has an amino acid sequence represented by a peptide consisting of Val-Pro-X (SEQ ID NO:1).

In this disclosure, Val (V) designates a valine residue, Pro (P) designates a proline residue, and X designates any of amino acid residues. These amino acid residues are preferably in L form.

While the aforementioned X is not limited particularly, it may, for example, be amino acid residues obtained from milk protein hydrolysates, and those selected from such amino acid residues are preferred. It is also preferable that the aforementioned X is any of 20 natural amino acids. A free amino acid is designated generally by "$H_3N-(R_1)CH-COO-$", and a peptide of the present disclosure can be designated also by "Val-Pro-HN—$(R_1)$CH—COOH".

The amino acid residue designated by the aforementioned X can be classified into an acidic amino acid residue, a basic amino acid residue, and a neutral amino acid residue. The aforementioned X can be one or more selected from the examples of the amino acid residues shown below.

The aforementioned acidic amino acid residue may, for example, be an aspartic acid residue (Asp(D)), a glutamic acid residue (Glu(E)), and the like. Among these, those each having 2 carbonyl groups are preferred.

The aforementioned basic amino acid residue may for example be a lysine residue (Lys(K)), an arginine residue (Arg(R)), a histidine residue (His(H)), and the like. Among these, those each having 2 to 4 amino groups are preferred.

The aforementioned neutral amino acid residue may for example be those whose $R_1$ in the aforementioned amino acid residue X is hydrogen and an alkyl group; hydroxy group; sulfur; acidic amide; aromatic group, and they may sometimes be referred to respectively as an aliphatic neutral amino acid residue; a hydroxy group-carrying neutral amino acid residue; a sulfur-carrying neutral amino acid residue; an amide group-carrying neutral amino acid residue; and an aromatic group-carrying neutral amino acid residue.

The aforementioned aliphatic neutral amino acid residue may, for example, be an alanine residue (Ala(A)), a glycine residue (Gly(G)), a valine residue (Val(V)), a leucine residue (Leu(L)), an isoleucine residue (Ile(I)), and the like. Among these, a hydrogen- or alkyl group-carrying neutral amino acid residue whose $R_1$ in the aforementioned amino acid residue X is hydrogen or an alkyl group is preferred. This alkyl group is preferably a straight or branched chain, with a branched chain being more preferred. The number of carbon atoms in $R_1$ in the aforementioned aliphatic neutral amino acid residue is preferably 0 to 4 and more preferably 0 to 3. A further preferable one has $R_1$=hydrogen, a methyl group (—$CH_3$), or an isopropyl group (—$CH(CH_3)_2$).

The aforementioned hydroxy group-carrying neutral amino acid residue may, for example, be a serine residue (Ser(S)), a threonine residue (Thr(T)), and the like. The $R_1$ in the aforementioned amino acid residue X is preferably a hydroxy group-carrying C1-2 alkyl group.

The aforementioned sulfur-carrying neutral amino acid residue may, for example, be a cysteine residue (Cys(C)), a methionine residue (Met(M)), and the like.

The aforementioned amide group-carrying neutral amino acid residue may, for example, be a glutamine residue (Gln(Q)), an asparagine residue (Asn(N)), and the like. Among these, one having 2 amino groups is preferred. The $R_1$ in the aforementioned amino acid residue X is preferably an amide group-carrying C1-2 alkyl group.

The aforementioned aromatic group-carrying neutral amino acid residue may, for example, be a phenyl alanine residue (Phe(F)), a tyrosine residue (Tyr(Y)), a tryptophan residue (Trp(W)), and the like. The $R_1$ in the aforementioned amino acid residue X is preferably an optionally hydroxy group-carrying benzyl group (for example, HO—$C_6H_4$—$CH_2$— or H—$C_6H_4$—$CH_2$— and the like), and the number of hydroxy groups here is preferably 0 to 1.

Among the amino acid residues described above, the basic amino acid residue and the neutral amino acid residue are preferred. Among the aforementioned neutral amino acid residues, those which are more preferable are an aliphatic neutral amino acid residue, a hydroxy group-carrying neutral amino acid residue, an amide group-carrying neutral amino acid residue, and an aromatic group-carrying neutral amino acid residue. Those which are further preferable are the aliphatic neutral amino acid residue and the amide group-carrying neutral amino acid residue.

Among the amino acid residues represented by the aforementioned X, one selected from an alanine residue, a glutamine residue, a methionine residue, an asparagine residue, a glycine residue, a valine residue, a tyrosine residue, a serine residue, and a lysine residue is preferred. Among these, the alanine residue, the glutamine residue, the asparagine residue, the glycine residue, the valine residue, the tyrosine residue, and the serine residue are preferred. Also, from the viewpoint of the bioactivity, the alanine residue, the glutamine residue, and the valine residue are preferred.

Those preferred from the viewpoint of the dipeptidyl peptidase-IV inhibiting activity are the alanine residue, the glutamine residue, the asparagine residue, the glycine residue, the valine residue, the tyrosine residue, the serine residue, and the lysine residue, while those especially preferred from the viewpoint of the angiotensin converting enzyme inhibiting activity are the alanine residue and the lysine residue.

Those which are exemplified also as novel peptides of the present disclosure may, for example, be the peptides consisting of the following amino acid sequences.

Examples are tripeptides such as Val-Pro-Ala (VPA: SEQ ID NO:2), Val-Pro-Gln (VPQ: SEQ ID NO:3), Val-Pro-Met (VPM: SEQ ID NO:4), Val-Pro-Asn (VPN: SEQ ID NO:5), Val-Pro-Gly (VPG: SEQ ID NO:6), Val-Pro-Val (VPV: SEQ ID NO:7), Val-Pro-Tyr (VPY: SEQ ID NO:8), Val-Pro-Ser (VPS: SEQ ID NO:9), Val-Pro-Lys (VPK: SEQ ID NO:10) and the like.

The salts of these peptides may also be employed as peptides of the present disclosure. Such salts may, for example, be those of alkaline metals such as potassium and sodium; alkaline earth metals such as calcium and magnesium, one or two or more of which may appropriately be employed.

The method for producing a peptide VPX of the present disclosure can be conducted in accordance with the method described for example in Pamphlet of International Publication WO 2003/044044 [Reference 1], and may, for example, be the following method, which is not limitative.

For example, those which can be exemplified are a method in which a protein or peptide containing an amino acid sequence represented by Val-Pro-X (SEQ ID NO:1) or an amino acid sequence represented by any of the tripeptides herein is degraded by hydrolysis to obtain degradation products which is then subjected to separation and purification; a method in which a peptide VPX is synthesized by a chemical peptide synthesis to obtain synthesized products from which the peptide VPX is separated and purified; a method in which a plant, animal, or microorganism producing the peptide VPX or a peptide containing the same is extracted and the resultant extract is subjected to separation and purification, and the like.

The peptide VPX of the present disclosure can be produced, for example, by hydrolyzing a protein such as casein with an acid, an alkaline, an enzyme, and the like, as appropriate.

A method for obtaining the aforementioned peptide VPX by hydrolyzing a starting protein with a hydrolase is exemplified.

First, a starting protein is dissolved, dispersed, or suspended in water prior to hydrolysis with an enzyme.

The aforementioned starting protein is not limited particularly as long as it is a VPX-containing protein and it can form a peptide of the present disclosure when being digested with a hydrolase as appropriate. The aforementioned protein may for example be those derived from animals or microorganisms, and is preferably a casein which can be obtained in a large amount.

When the starting protein here is soluble, then the starting protein may be dispersed in water or warmed water and dissolved, although the procedure may vary depending on the nature of the starting protein, and when hardly soluble, then the protein is placed in hot water and homogenized by agitation.

It is also possible that the aforementioned protein-containing solution is combined with an alkali reagent or an acid reagent to adjust the pH as appropriate (for example, pH 7 to 10). This pH is adjusted preferably at or around the optimum pH of the hydrolase employed.

The aforementioned alkali reagent or acid reagent is not limited particularly, and an ingestible or pharmaceutically acceptable one may be employed. The alkali reagent may, for example, be a hydroxide such as sodium hydroxide or calcium hydroxide; a carbonate such as potassium carbonate, which may be an alkali metal salt or alkali earth metal salt. The acid reagent may, for example, be an inorganic acid such as hydrochloric acid, phosphoric acid, or the like; an organic acid such as citric acid, acetic acid, formic acid, and the like. Among these, one or two or more may be employed as appropriate.

It is also desirable, from the viewpoint of protection from contamination-induced deterioration, that the solution containing the aforementioned protein be subjected to a heat sterilization at 70 to 90° C. for 15 seconds to 10 minutes.

Subsequently, the aforementioned protein-containing solution is combined with a predetermined amount of a hydrolase, and reacted at a temperature of about 10 to 85° C. for 0.1 to 48 hours to obtain a hydrolysate.

Here it is desirable that, after adding the aforementioned hydrolase, the relevant solution is kept at a suitable temperature depending on the type of the enzyme, for example 30 to 60° C., desirably 45 to 55° C., and then the hydrolysis of the protein is started.

The hydrolytic reaction time is a time during which the reaction is continued until a preferable degradation ratio is achieved while monitoring the degradation ratio of the enzymatic reaction. The degradation ratio of the aforementioned starting protein is desirably 20 to 55% for obtaining a peptide of the present disclosure.

The termination of the aforementioned hydrolase reaction is accomplished, for example, by inactivation of the enzyme in the hydrolysis solution, and can be conducted by an ordinary heat inactivation treatment. The heating temperature and the duration of the heat inactivation treatment may be set as appropriate at a condition allowing for a sufficient inactivation while taking the thermal stability of the enzyme employed into consideration, and may for example be a temperature within the range of 80 to 130° C. and a duration from 2 seconds to 30 minutes.

While the aforementioned hydrolase is not limited particularly, it is preferably an enzyme having an ability of forming a peptide of the present disclosure by hydrolyzing the aforementioned starting protein, and a preferable enzyme having such an ability is typically an endopeptidase.

The aforementioned endopeptidase may for example be those derived from microorganism or from animals, and may typically be proteases derived from bacteria of the genus of *Bacillus* or *Aspergillus*, or proteases derived from animal pancreas. The aforementioned proteases can be those which are commercially available. As a preferable commercially available protease, a protease derived from a bacterium of the genus of *Aspergillus* such as protease A (manufactured by Amano Enzyme Inc.) and the like and a protease derived from animal pancreas such as pancreatin (manufactured by Amano Enzyme Inc.) can be utilized.

For example, when a protease derived from a bacterium of the genus of *Aspergillus* is used, it is added preferably at a proportion of 100 to 5000 activity units to 1 g of the protein. When a protease derived from an animal pancreas is used, it is added preferably at a proportion of 3000 to 8000 activity units to 1 g of the protein.

The hydrolase employed in this disclosure can be employed alone or in combination with two or more. When two or more enzymes are employed, their respective enzymatic reactions can be conducted simultaneously or separately.

In this disclosure, a pancreatin and a protease are used preferably in combination, and these two enzymes are used most preferably in a mixture with each other.

The degradation ratio of the starting protein is calculated by measuring the total nitrogen quantity of a sample by the Kjeldahl method (Ed. by Japanese Society for Food Science and Technology, "SHOKUHINBUNSEKIHO (Food analysis method)", page 102, Published by Korin Publishing Co., Ltd., 1984) and then measuring the formol nitrogen quantity of the sample by the formol titration method (Mitsuda et al., "SHOKUHINKOGAKU JIKKENSHO (Experiments in food science and technology)", 1st Vol., page 547, Yokendo Co., Ltd., 1970), followed by using the measured values thus obtained to calculate the degradation ratio according to the following equation.

$$\text{Degradation ratio (\%)} = (\text{formol nitrogen quantity} / \text{total nitrogen quantity}) \times 100$$

It is preferable that from the aforementioned hydrolysate solution the peptide VPX of the present disclosure is isolated or purified.

The purification of the peptide VPX of the present disclosure can be conducted by combining procedures similar to those employed ordinarily for the purification of oligopeptides, such as various chromatographic methods including, for example, ion exchange chromatography, adsorption chromatography, reverse phase chromatography, partition chromatography, gel filtration chromatography, and the like, solvent precipitation, salting out, partition between two liquid phases, like, as appropriate.

When conducting the isolation or the purification of the peptide VPX of the present disclosure, the fraction containing the intended substance can be determined by using as an index the dipeptidyl peptidase-IV inhibiting effect and/or angiotensin converting enzyme inhibiting effect described below. The active ingredient in such a fraction can be identified by a mass spectrometry.

The protein degradation product obtained by the hydrolase is preferably one containing at least VPX, and one prepared to contain the amino acid sequence represented by any of the tripeptides named herein is further preferred because a further favorable active ingredient can readily be recovered.

The peptide VPX of the present disclosure can be produced also by a chemical synthesis.

The chemical synthesis of the peptide VPX of the present disclosure can be conducted by a liquid phase method or a solid phase method employed ordinarily in the synthesis of oligopeptides. The synthesized peptide can be deprotected if necessary and made free of unreacted reagents or by-products, thereby isolating the peptide VPX of the present disclosure.

Such a peptide synthesis can be conducted using a commercially available peptide synthesis instrument. It can be confirmed that the intended peptide was obtained using as an index the dipeptidyl peptidase-IV inhibiting effect and/or angiotensin converting enzyme inhibiting effect described below.

The peptide VPX of the present disclosure has a dipeptidyl peptidase-IV inhibiting effect as shown in Examples described below.

As a result of the degradation of compounds associated with in vivo physiological functions by the dipeptidyl peptidase-IV, various diseases or symptoms may occur. Accordingly, by utilizing the dipeptidyl peptidase-IV inhibition thereby prolonging the life of an in vivo physiological function-associated compound which is usually decomposed by the dipeptidyl peptidase-IV, the prophylaxis, improvement, or therapy of the dipeptidyl peptidase-IV-induced disease or symptoms becomes possible.

The aforementioned physiological function-associated compound may for example be incretin's glucagon-like peptide-1 (GLP-1) and glucose-dependent insulinotropic polypeptide (GIP). As a result of suppression of the degradation of this incretin's glucagon-like peptide-1, various effects can be exerted such as insulin biosynthesis- and secretion-responsive glucose inducible stimulation, glucagon secretion suppression, gene expression regulation, B-cell trophic effect, food intake suppression, and gastric content output slowing.

As a result, contribution to normalization of once elevated blood sugar level, as well as improvement and regulation of hunger and body weight can be achieved.

It is also known that the effect of the dipeptidyl peptidase-IV serves to reduce the vascular endothelial cell function and to impair the vascular endothelial cell. Such a reduced function or impairment of this vascular endothelial cell leads diabetes complications such as vascular disorders including vasohypertonic vasoconstriction, arteriosclerosis, thrombus formation, and the like, which are causative of organ bloodstream disorders and organ dysfunction.

Recently, the endothelial cell function improving effect of the treatment with a dipeptidyl peptidase-IV inhibiting drug was reported in a large number of documents (for example, see References 2 to 5 [Reference 2] Endocrine Journal 2011, 58 (1), 69-73; [Reference 3] J Am Coll Cardiol. 2012, 59(3), 265-76; [Reference 4] Diabetes Care. 2011, 34(9), 2072-7; [Reference 5] Cardiovascular Diabetology 2011, 10(85) (http://www.cardiab.com/content/10/1/85)).

Such an effect is considered to be mediated not only by the improvement due to just a reduction in the blood sugar level but also by the incretin's blood vessel protecting effect. Once the flexibility of a blood vessel is lost due to the high blood sugar-induced endothelial cell dysfunction, the blood pressure is elevated, and the elevated blood pressure then further injures the blood vessel to give a vicious circle, which is realized as an adverse effect on organs such as heart, kidney, and brain. In order to break this vicious circle, a combination of a dipeptidyl peptidase-IV inhibiting drug and an angiotensin converting enzyme inhibiting drug is administered. It is considered that the dipeptidyl peptidase-IV inhibitor plays an important role also in the therapy of circulation system.

Thus, since the peptide VPX of the present disclosure has a dipeptidyl peptidase-IV inhibiting effect, it exhibits blood sugar rise suppressing effect, hyperglycemia improvement effect, vascular endothelial dysfunction suppressing effect, vascular endothelial disorder suppressing effect, vascular disorder suppressing effect, vascular endothelial cell protecting effect, anorectic effect, and the like. Furthermore, the peptide VPX of the present disclosure are considered to allow for anorectic action, and vascular endothelial cell protection, and the like. As used herein, "blood sugar rise suppression" has a meaning including blood sugar reduction, and especially means that "capability of reducing the blood sugar level once exceeding a normal level or elevating unnecessarily". For the judgment of a normal blood sugar level, see the diagnostic criteria in 2010 of The Japan Diabetes Society.

Moreover, it is considered that by inhibiting the dipeptidyl peptidase-IV with the peptide VPX of the present disclosure prophylaxis, improvement, or therapy of the dipeptidyl peptidase-IV-induced disease or symptoms becomes possible. Accordingly, the peptide VPX of the present disclosure can be used in a method intending to accomplish prophylaxis, improvement, and/or therapy of the dipeptidyl peptidase-IV-induced disease or symptoms and the like via ingestion or administration by other means in animals, including humans.

Various diseases or symptoms caused by the dipeptidyl peptidase-IV of the present disclosure may for example be a hyperglycemic disease, diabetes, a diabetes complication, a vascular endothelial disorder, a vascular disorder, and the like. The dipeptidyl peptidase-IV-induced various diseases and the like may also be the dipeptidyl peptidase-IV-mediated various diseases and the like.

In addition the hyperglycemic disease, such as diabetes, and hyperglycemic states-induced various diseases diabetic microangiopathy (for example, retinopathy, nephropathy, neuropathy) and a great vessel complication (for example, ischemic disease such as angina pectoris/myocardial infarction, cerebral infarction, obstructive arteriosclerosis, necropathy), can be ameliorated.

With regard to the fact that the dipeptidyl peptidase-IV inhibitor can be employed in the treatment of aforementioned various diseases as a prophylactic agent or a therapeutic agent, the disclosures of the aforementioned Patent Documents 1 to 5 and References 2 to 5 can be referred to, and it is a matter of course that the peptide VPX of the present invention can also be practiced in the aforementioned various diseases as a prophylactic agent or a therapeutic agent.

Accordingly, the peptide VPX of the present disclosure may be administered for the aforementioned dipeptidyl peptidase-IV inhibition, blood sugar rise suppression, hyperglycemia improvement, vascular endothelial disorder suppression, anti-diabetic effect, and the like, and can also be employed in various formulations aiming at the aforementioned use, such as a dipeptidyl peptidase-IV inhibitor, a blood sugar rise suppressing agent, a vascular endothelial disorder suppressing agent, an anti-diabetic agent, and can be employed for producing appropriate formulations.

The peptide VPX of the present disclosure sometimes possesses, as indicated in Examples described below, an angiotensin converting enzyme (hereinafter referred to also as "ACE") inhibiting effect.

As used herein, the angiotensin converting enzyme is an enzyme which acts on angiotensin I generated from angiotensinogen as a result of cleavage by renin to release 2 amino acids at the C-terminal thereby accomplishing the conversion into angiotensin II.

While the angiotensin converting enzyme allows angiotensin II having a potent vasopressor effect to be generated, it also has an ability of inactivating bradykinin which has a hypotensive effect. Accordingly, the angiotensin converting enzyme inhibitor has already been employed as a therapeutic drug for hypertension, and there are pharmaceuticals employing Captopril, Renivace, and the like. Nevertheless, Captopril and Renivace sometimes exhibit an excessive hypotensive effect or a renal dysfunction as a side effect. As a result, a substance which is highly safe even when given as a supplement or a food additive, is desired. A large number of searches for substances having the angiotensin converting enzyme inhibiting effect have been reported (see References 1, 6 to 8. [Reference 1] Pamphlet of International Publication WO 2003/044044; [Reference 6] JP-A No. H06-40944; [Patent Document 7] JP-A No. 2001-136995; [Reference 8] JP-A No. H07-101982).

For example, References 6 and 7 reported that Val-Pro-Pro and Ile-Pro-Pro obtained by degrading a casein and the like with a *lactobacillus* or a combination of a proteinase and a peptidase have the angiotensin converting enzyme inhibiting effect. Otherwise, a tripeptide having the angiotensin converting enzyme inhibiting effect reported in Reference 8 is Leu-Leu-Trp and that in Reference 1 is Met-Lys-Pro.

It is considered that inhibition of the angiotensin converting enzyme allows the hypotensive effect and the bradykinin inactivating effect as well as the hypercardia recessing effect, the peripheral vasodilating effect, the kidney protecting effect, the substance P degradation suppressing effect, and the like to be exerted, and also allows the hypertensive state-induced vascular endothelial disorder suppressing effect, the vascular disorder suppressing effect, and the like to be exerted. It is also known that the angiotensin converting enzyme inhibitor is effective in improvement of essential hypertension.

In addition, it is also considered that inhibition of the angiotensin converting enzyme allows prophylaxis, improvement, or therapy of the angiotensin converting enzyme-induced disease or symptom to be achieved.

The angiotensin converting enzyme-induced disease or symptoms may for example be hypertension, hypercardia, renal hypertrophy, and the like. The angiotensin converting enzyme-induced various diseases and the like may be the angiotensin converting enzyme-mediated various diseases and the like.

The hypertension or hypertensive state-induced various diseases or symptoms may for example be cardiovascular diseases or vascular disorders such as cerebral hemorrhage, cerebral infarction, angina pectoris, myocardial infarction, renal failure, vision disorder, angioedema, and the like.

Thus, since the peptide VPX of the present disclosure has the angiotensin converting enzyme inhibiting effect, it exhibits the aforementioned hypotensive effect, bradykinin inactivating effect, hypertensive symptom improving effect, hypertensive state-induced vascular endothelial disorder suppressing effect, vascular disorder suppressing effect, and the like. Moreover, it is considered that by inhibiting the angiotensin converting enzyme with the peptide VPX of the present disclosure prophylaxis, improvement, or therapy of the aforementioned angiotensin converting enzyme-induced disease or symptoms become possible. Accordingly, the peptide VPX of the present disclosure can be used in a method intending to accomplish prophylaxis, improvement, and/or therapy of the angiotensin converting enzyme-induced disease or symptoms and the like via ingestion or administration thereof in animals including human.

With regard to the fact that the angiotensin converting enzyme inhibitor can be employed in the aforementioned various diseases as a prophylactic agent or a therapeutic agent, the disclosures of the aforementioned Patent Documents 1 and 6 to 8 can be referred to, and it is a matter of course that the peptide VPX of the present disclosure can also be practiced in the aforementioned various diseases as a prophylactic agent or a therapeutic agent.

Accordingly, the peptide VPX of the present disclosure may be administered for angiotensin converting enzyme inhibition, hypotensive treatment, hypertension, and the like, and can also be employed in various formulations aiming at the aforementioned use, such as an angiotensin converting enzyme inhibitor, a hypotensive agent, an antihypertensive agent, and the like, and can be employed for producing such various formulations.

Moreover, the peptide VPX of the present disclosure can be provided as a further beneficial compound when it possesses both efficacies, namely, the blood sugar rise suppressing effect and the hypotensive effect.

While a prolonged duration of a hyperglycemic level results in a reduced vascular endothelial function by which a vascular endothelial disorder tends to be induced readily, a high blood pressure, which poses a great load on such a blood vessel, is known to increase the risk of inducing the vascular disorder. The vascular endothelial cell produces vascular smooth muscle-relaxation factors (NO and PGI2). When the hyperglycemia reduces the vascular endothelial cell function, the ability of releasing such factors is also reduced. As a result, the diabetic patient allows hypertension to occur as a complication. Then the high blood pressure poses a load on the vascular endothelial cell, resulting in a vicious circle.

A human having diabetes or candidate thereof (this candidate means a human who has not have diabetes yet but in a condition of a hyperglycemic level) should be careful of the hypertension. Nevertheless, it is considered generally that a reduction of the blood sugar level administering a hyperglycemia improving drug cannot serve to reduce the blood pressure, and it is also considered on the other hand that a reduction of the blood pressure administering a hypotensive drug cannot serve to reduce the blood sugar. Accordingly, a human having both of diabetes and hypertension is treated frequently with both of the hyperglycemia improving drug and the hypotensive drug, which raises a concern of side effects due to the combination of the drugs.

Since the possession of these efficacies at a same time also enables a reduction in the quantity of the drugs to be used, the side effects are expected to be reduced.

Thus, the peptide VPX of the present disclosure is extremely effective in vascular improvement, vascular endothelial disorder suppression, and prophylaxis, improvement, or therapy of diabetes, and effective especially in prophylaxis, improvement, or therapy of hyperglycemic state-induced vascular endothelial disorder.

Typical diseases and symptoms of the vascular endothelial disorder of the present disclosure may for example be diabetic vascular disorder and the like.

As described above, the peptide VPX of the present disclosure and the aforementioned various formulations containing the same as an active ingredient (hereinafter referred to as "the aforementioned dipeptidyl peptidase-IV inhibitor and the like") can be used in a method intending to accomplish prophylaxis, improvement, and/or therapy of the aforementioned hyperglycemic disease, diabetes (especially type II diabetes), hypertension and diabetes complication (for example, diabetic vascular endothelial disorder or nephropathy, hypertension and the like), vascular endothelial disorder, vascular disorder, and the like via ingestion or administration thereof in animals including human.

Also the aforementioned various formulations containing the peptide VPX of the present disclosure as an active ingredient can be used in a method intending to accomplish prophylaxis, improvement, and/or therapy of the aforementioned hyperglycemic disease, diabetes (especially type 2 diabetes) and diabetes complication(for example, diabetic vascular endothelial disorder or nephropathy, hypertension, and the like), vascular endothelial disorder, vascular disorder, and the like via ingestion or other means of administration thereof in animals including human.

In addition, the peptide VPX of the present disclosure and the aforementioned various formulations containing the same as an active ingredient can be used as being incorporated as an active ingredient in pharmaceuticals, quasi drugs, topical dermal formulations, cosmetics, foods, and the like for human or animals for prophylaxis, improvement, and/or therapy of the aforementioned hyperglycemic disease, diabetes, vascular disorder, hypertension, and the like.

Upon incorporation in a pharmaceutical, an orally administrable agent or a parenterally administrable agent can be employed. Also upon incorporation in a food, utilization is possible in functional foods, foods for patients, foods for specified health uses, and the like having biological functions as their own concepts such as prophylaxis, improvement, or therapy of the aforementioned dipeptidyl peptidase-IV-induced various diseases and/or angiotensin converting enzyme-induced various diseases, as well as hyperglycemic state and/or hypertension-induced various diseases and the like, dipeptidyl peptidase-IV inhibition, blood sugar rise suppression, hyperglycemia improvement, angiotensin converting enzyme inhibition, hypotensive treatment, and the like.

The peptide VPX of the present disclosure and the aforementioned various formulations containing the same as an active ingredient can be used as being incorporated as an active ingredient in pharmaceuticals, quasi drugs, topical dermal formulations, cosmetics, foods, and the like for human or animals for prophylaxis, improvement, and/or therapy of the aforementioned hyperglycemic disease, diabetes, hypertension, vascular disorder, and the like.

While the peptide VPX of the present disclosure and the aforementioned various formulations containing the same as an active ingredient may be given by oral administration or parenteral administration, the oral administration is desirable. Those which can be exemplified for the parenteral administration are intravenous infusion, rectal administration, aspiration, and the like. Those which can be exemplified as dosage forms for oral administration are tablet, capsule, troche, syrup, granule, acid reagents, ointment, and the like.

The formulating procedure can employ, in addition to milk protein hydrolysates or the peptide VPX of the present disclosure, the components employed usually in the formulation procedure, such as an excipient, a pH regulating agent, coloring agent, flavoring agent, and the like. Use at the same time with a drug having the dipeptidyl peptidase-IV inhibiting effect and/or angiotensin converting enzyme inhibiting effect, anti-diabetic drug, hyperglycemia improving drug, hypotensive drug, and the like, which is known or will be known in future, is also possible.

It is also possible to allow the peptide VPX of the present disclosure to be contained as an active ingredient in a food and processed, as one embodiment of the peptide VPX of the present disclosure and the aforementioned various formulations containing the same as an active ingredient, into a food having a dipeptidyl peptidase-IV effect and/or an angiotensin converting enzyme inhibiting effect.

Such a food, regardless of the form such as liquid, paste, solid, powder, and the like, may for example be tablet candies, liquid foods, feeds (including those for companion animals), and the like, as well as flour products, instant foods, processed agricultural products, processed marine products, processed livestock products, milk and dairy products, fats, basic seasonings, composite seasonings and foods, frozen foods, beverages, other commercially available products, and the like.

The aforementioned flour products may for example be breads, macaroni, spaghetti, noodles, pancake mixes, deep-frying flours, bread crumbs, and the like. The aforementioned instant foods may for example be instant noodles, pot noodles, retort/ready-to-eat foods, ready-to-eat canned foods, microwave foods, instant soups and stews, instant miso soups/broths, canned soups, freeze-dried foods, other instant foods, and the like.

The aforementioned processed agricultural products may for example be canned agricultural products, canned fruits, jams and marmalades, pickles, boiled beans, dried agricultural products, cereal foods (processed cereals), and the like. The aforementioned processed marine products may for example be canned marine products, fish hams/sausages, boiled fish pastes, marine delicacies, soy sauce-boiled sweetened foods, and the like. The aforementioned processed livestock products may for example be canned livestock products/pastes, livestock hams/sausages, and the like.

The aforementioned milk and dairy products may for example be processed milks, milk beverages, yogurts, *lactobacillus* beverages, cheeses, ice creams, formulated powder milks, creams, other dairy products, and the like. The aforementioned fats may for example be butters, margarines, vegetable fats, and the like.

The aforementioned basic seasonings may for example be soy sauces, miso, sauces, processed tomato seasonings, sweet sake seasonings, vinegars and the like, and the aforementioned composite seasonings and foods may for example be cooking helper mixes, curry helpers, seasoned sauces, dressings, noodle dip sauces, spices, other composite seasonings, and the like.

The frozen food may for example be frozen raw foods, half-cooked frozen foods, cooked frozen foods, and the like.

The aforementioned confectioneries may for example be caramels, candies, chewing gums, chocolates, cookies, biscuits, cakes, pies, snacks, crackers, Japanese confectioneries, rice confectioneries, pea confectioneries, dessert confectioneries, other confectioneries, and the like.

The aforementioned beverages may for example be carbonated beverage, natural fruit juice, fruit juice beverage, fruit juice-containing soft-drink beverage, fruit pulp beverage, fruit granule-containing fruit beverage, vegetable-based beverage, soy milk, soy milk beverage, coffee beverage, green tea beverage, powdered beverage, concentrated beverage, sports beverage, nutrition beverage, alcohol beverage, other luxury beverage, and the like.

Commercially available foods other than those listed above may for example be baby foods, rice topping "Furikake", submerged rice seaweed topping "Ochazuke-nori", and the like.

In the dipeptidyl peptidase-IV inhibitor and the like of the present disclosure, the quantity of the peptide VPX of the present disclosure to be incorporated is preferably at least 0.001% by mass based on the final composition of the formulation.

The dose of the peptide VPX of the present disclosure may vary depending on the age, symptoms, and the like, and is usually 0.001 to 3000 mg/day, and preferably 0.01 to 30 mg/day, which may be given as being divided into 1 to 3 portions in a single day.

EXAMPLES

The followings are typical examples and the like, to which the present invention (present disclosure) is not limited.

Production Example 1

Peptide VPX Production by Casein Enzymolysis

<1> Casein Enzymolysis 100 g of a commercially available casein (manufactured by New Zealand Dairy Board) was combined with 900 g of water, dispersed thoroughly, adjusted at pH 7.0 by adding sodium hydroxide to the solution, thereby dissolving the casein completely. This casein aqueous solution was sterilized by heating at 85° C. for 10 minutes, adjusted at a temperature of 50° C., and adjusted at pH 9.0 by adding sodium hydroxide, and thereafter 2 g of pancreatin (manufactured by Amano Enzyme Inc.) and 4 g of protease A (manufactured by Amano Enzyme Inc.) were added to initiate the hydrolytic reaction. At the time when the degradation ratio of the casein reached 54.9%, the enzyme was inactivated by heating at 80° C. for 6 minutes to terminate the enzymatic reaction, followed by cooling to 10° C. This hydrolysis solution was filtered through kieselguhr, concentrated and then freeze-dried to obtain 80 g of a freeze-dried material.

<2> Peptide Separation by HPLC

A reverse phase HPLC was employed to separate the aforementioned casein hydrolysate. The condition of this HPLC was indicated in HPLC Condition 1 shown below.

[HPLC Condition 1]
Column: Cadenza CD-C18
10 mmI.D.×250 mm (manufactured by Intact Corp.)
Detection: UV 215 nm
Flow rate: 3 ml/minute
Eluent A: 0.2% FA-containing aqueous solution
Eluent B: 0.2% FA-containing acetonitrile solution Under a gradient condition starting from an Eluent A level of 98%, followed by 75% after 30 minutes, followed by 50% after 40 minutes, followed by 20% after 43 minutes, the hydrolysate was separated and the effluent was fractionated every 0.75 ml. The eluted fractions were subjected to a measurement of the dipeptidyl peptidase-IV inhibiting ability, and the fraction eluted at a retention time of 16.5 minutes (Fraction 1) exhibited a potent inhibition-active ability.

For further purification, HPLC under another condition was employed for purification. The condition at this time is indicated in the HPLC condition 2 shown below. At this time the Eluents A and B in Condition 1 were changed to Eluents A and B in Condition 2, respectively, while other parameters were similar to those in Condition 1.

[HPLC Condition 2]
Column: Cadenza CD-C18
10 mmI.D.×250 mm (manufactured by Intact Corp.)
Detection: UV 215 nm
Flow rate: 3 ml/minute
Eluent A: 0.1% TFA-containing aqueous solution
Eluent B: 0.1% TFA-containing acetonitrile solution Under the same gradient condition, the hydrolysate was separated and the effluent was fractionated every 0.75 ml. The eluted fractions were subjected to a measurement of the dipeptidyl peptidase-IV inhibiting ability, and Fraction 2 eluted at a retention time of 23.0 minutes and Fraction 3 eluted at a retention time of 22.0 minutes exhibited potent inhibition-active abilities. Fraction 2 had a concentration for 50% inhibition of the enzymatic activity of 2.0 μg/ml.

The compound in Fraction 2 having the aforementioned activity peak was subjected to identification by Protein Sequencer (PPSQ-23A) manufactured by Shimadzu Corporation. As a result, it was revealed to have a novel structure Val-Pro-Ala (SEQ ID NO:2). These amino acid residues had L forms.

Furthermore, a mass spectrometer LTQ manufactured by ThermoQuest Corporation exhibited a molecular weight of 285.2, and an MS/MS analysis using m/z=286.2 (MH+) as a precursor ion detected product ions such as m/z=169.3, 187.2, 197.1 and the like as shown in FIG. 1.

As a result, the structure of the peptide having an ability of inhibiting the dipeptidyl peptidase-IV was proven to be Val-Pro-Ala.

The 50% inhibition concentration of the synthetic peptide VPA (SEQ ID NO:2) obtained in Example 2 described below was 1.9 μg/ml, which was in agreement with the value of the purified fraction.

Figure 2:
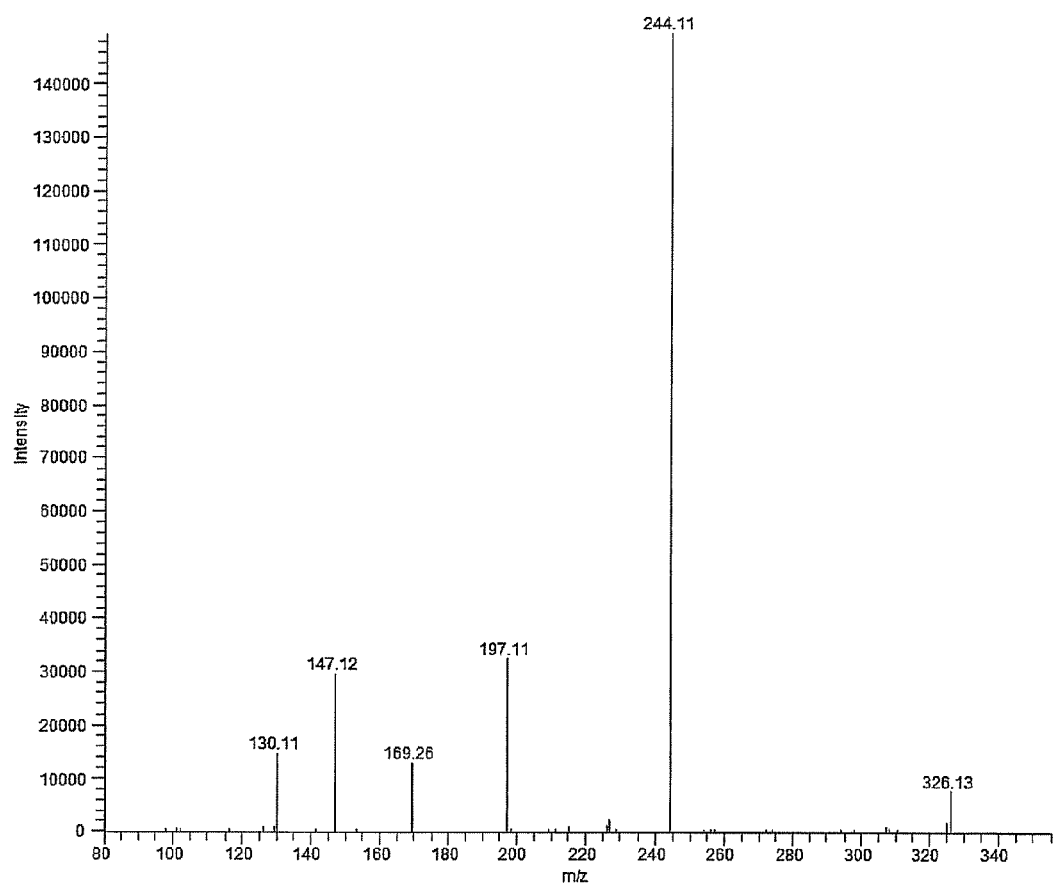
FIG. 2 is a schematic view showing the results of the MS/MS analysis of the peptide VPQ of the present disclosure.

The compound in Fraction 3 having the aforementioned activity peak was also subjected to similar identification, and it was revealed to have a novel structure Val-Pro-Gln (SEQ ID NO:3) (molecular weight: 342.2), as shown in FIG. 2. All of these amino acid residues had L forms.

Accordingly, it was confirmed that in the aforementioned <1> Casein hydrolysate, VPA (SEQ ID NO:2) and VPQ (SEQ ID NO:3) were contained as novel peptides having the dipeptidyl peptidase-IV inhibiting activity.

In addition, it was confirmed that the aforementioned <1> Casein hydrolysate possessed the dipeptidyl peptidase-IV inhibiting activity and its degradation products contained VPV (SEQ ID NO:7), VPY (SEQ ID NO:8), VPK (SEQ ID NO:10). All of these amino acid residues had L forms.

Production Example 2

Chemical Synthesis of VPX Peptide

Using a peptide synthesizer (Model 433A type, Applied Biosystems) and Fmoc-Val (Peptide Institute Inc.), Fmoc-Pro (Peptide Institute Inc.), and Fmoc-Ala-Wang-PEG Resin (Watanabe Chemical Industries Ltd.) as starting materials, a tripeptide Val-Pro-Ala was synthesized by a solid phase synthesis method.

The operation was conducted in accordance with the instruction of Applied Biosystems, and thereafter deprotection was conducted. This peptide was purified under the aforementioned HPLC Condition 1.

The resultant tripeptide was measured by the mass spectrometry to have a molecular weight (M) of 285.2, and an MS/MS analysis using m/z=286.2 (MH+) as a precursor ion exhibited a spectrum similar to the spectrum of the purified fraction. VPQ (SEQ ID NO:3) was also prepared similarly, and it exhibited a spectrum similar to the spectrum of the purified fraction (Mass spectrometry exhibited a molecular weight (M) of 342.2).

Also for VPM (SEQ ID NO:4), VPN (SEQ ID NO:5), VPG (SEQ ID NO:6), VPV (SEQ ID NO:7), VPY (SEQ ID NO:8), VPS (SEQ ID NO:9), and VPK (SEQ ID NO:10), the operation in accordance with Production Example 2 was conducted to synthesize these peptides chemically.

Test Example 1

Verification Test for Dipeptidyl Peptidase-IV Inhibiting Activity of Each Peptide Each peptide shown in Table 1 which was obtained in Production Example 2 was subjected to a verification test for the dipeptidyl peptidase-IV inhibiting activity and the results are shown in Table 1.

TABLE 1

| Each peptide | Test Example 1: DPP-4 inhibiting activity $IC_{50}(\mu g/ml)$ |
|---|---|
| VPA (SEQ ID NO:2) | 1.9 μg/ml |
| VPQ (SEQ ID NO:3) | 2.6 μg/ml |
| VPN (SEQ ID NO:5) | 5.7 μg/ml |
| VPG (SEQ ID NO:6) | 3.4 μg/ml |
| VPV (SEQ ID NO:7) | 1.0 μg/ml |
| VPY (SEQ ID NO:8) | 7.15 μg/ml |
| VPS (SEQ ID NO:9) | 5.17 μg/ml |
| VPK (SEQ ID NO:10) | 10.4 μg/ml |
| VPP (SEQ ID NO:11) | >2000 μg/ml |
| IPP (SEQ ID NO:12) | 1342 μg/ml |
| LY (SEQ ID NO:13) | 486 μg/ml |

Test Example 2

Verification Test for Angiotensin Converting Enzyme Inhibiting Activity of Each Peptide VPA (SEQ ID NO:2) and VPK (SEQ ID NO:10) were subjected to the verification test for the ACE inhibiting activity, and were revealed to have 50% inhibition concentrations of 24.8 μg/ml and 132 μg/ml, respectively. Thus, since these VPA and VPK possess both of the dipeptidyl peptidase-IV inhibiting effect and the angiotensin converting enzyme inhibiting effect, they are considered to be extremely effective in vascular improvement, vascular endothelial disorder suppression, and prophylaxis, improvement, or therapy of diabetes.

Accordingly, a casein enzymolytic product containing at least one of these tripeptides (SEQ ID NO:2 to 10) is considered to be utilizable in foods, pharmaceuticals, and the like, as a raw material or a food material having the dipeptidyl peptidase-IV inhibiting effect, angiotensin converting enzyme inhibiting effect, and the like.

When searching for commercially available casein degradation product containing at least VPA, VPA was found in the casein degradation products of CU5000 (manufactured by Morinaga Milk Industry Co., Ltd.), which had a concentration for 50% inhibition of the dipeptidyl peptidase-IV of 84 μg/ml. On the other hand, C800 (manufactured by Morinaga Milk Industry Co., Ltd.) had a concentration for 50% inhibition of the dipeptidyl peptidase-IV of >1000 μg/ml, showing that some had no dipeptidyl peptidase-IV inhibiting activity in spite that they are casein hydrolysates.

<Method for Measuring Dipeptidyl Peptidase-IV Inhibiting Activity>

The measurement of the dipeptidyl peptidase-IV (DPP-4) inhibition was conducted in accordance with the method by Kato et al (Kato, T. et al. Biochem. Med. 19, p 351, 1978).

Typically, the enzymatic reaction was conducted using Recombinant Human DPPIV/CD26 (R&D Systems, Inc.) as an enzyme (DPP-4) and H-Gly-Pro-AMC (Biomol GmbH) as a substrate.

To each well of a 96-well microplate (nunc 137101), water or an aqueous solution of the test substance at each concentration or a HPLC fraction was added, and then 20 μl of Tris-HCl (0.25M, pH 8.0) was added to make the entire volume 80 μl. After stirring, the plate was warmed for about 10 minutes in an incubator at 37° C., and 10 μl of the DPP-4 solution and 10 μl of the substrate solution were added (a total volume of 100 μl), and stirred to initiate the reaction. The well receiving water instead of the enzyme was used as a control.

The enzymatic reaction was measured using a microplate reader (SH-9000, Corona Electric Co., Ltd), and the measurement was conducted under the condition which kept the temperature in the chamber at 37° C. (5-minute intervals, ex360 nm/em460 nm).

From the fluorescent intensity value during the time period during which the fluorescent intensity was increased linearly (within 30 minutes after initiation of the reaction), the inhibiting activity was calculated using the following equation. As a positive control, Vildagliptin (JS Research Chemicals Trading) was employed.

$$\text{Inhibition ratio } (\%) = 100\% - [(Y-b)/(X-a)] \times 100\%$$

X: Water+Enzyme+Substrate
Y: Test substance+Enzyme+Substrate
a: Water+Substrate
b: Test substance+Substrate <Method for Obtaining $IC_{50}$>

The test substance was diluted serially to several concentrations (10 to 2000 μg/ml), whose inhibition ratio was obtained. Based on these results, the equation of the relationship between the logarithmic value ($\log_{10}$) of the concentration of the added test substance and the inhibition ratio was obtained. Then from this equation of the relationship, the concentration allowing the enzyme inhibition ratio to be 50% was calculated reversely, thereby calculating the $IC_{50}$.

<Method for Measuring Angiotensin Converting Enzyme Inhibiting Activity>

The measurement of the angiotensin converting enzyme inhibition (ACE inhibition) was conducted in accordance with the method by Araujo et al [Araujo, M. C., et al., Biochemistry 39, 8519, 2000].

The enzymatic reaction was conducted using Angiotensin Converting Enzyme, from rabbit lung (SIGMA) as an enzyme (ACE) and Abz-FRK(Dnp)-P (Enzo Life Sciences International, Inc.) as a substrate (Araujo, M. C., et al., Biochemistry 39, 8519, 2000).

To each well of a 96-well microplate (nunc 137101), water or an aqueous solution of the test substance at each concentration or a HPLC fraction was added, and then 20 μl of Tris-HCl (0.25M, pH 8.0) was added to make the entire volume 80 μl. After stirring, the plate was warmed for about 10 minutes in an incubator at 37° C., 10 μl of the ACE solution and 10 μl of the substrate solution were added (a total volume of 100 μl), and stirred to initiate the reaction. The well receiving water instead of the enzyme was used as a control.

The enzymatic reaction was measured using a microplate reader (SH-9000, Corona Electric Co., Ltd), and the measurement was conducted under the condition which kept the temperature in the chamber at 37° C. (5-minute intervals, ex320 nm/em420 nm).

From the fluorescent intensity value during the time period during which the fluorescent intensity was increased linearly (within 30 minutes after initiation of the reaction), the inhibiting activity was calculated using the following equation.

$$\text{Inhibition ratio } (\%) = 100\% - [(Y-b)/(X-a)] \times 100\%$$

X: Water+Enzyme+Substrate
Y: Test substance+Enzyme+Substrate
a: Water+Substrate
b: Test substance+Substrate <Method for Obtaining $IC_{50}$>

The test substance was diluted serially to several concentrations (10 to 2000 μg/ml), whose inhibition ratio is obtained. Based on these results, the equation of the relationship between the logarithmic value ($\log_{10}$) of the concentration of the added test substance and the inhibition ratio was obtained. Then from this equation of the relationship, the concentration allowing the enzyme inhibition ratio to be 50% was calculated reversely, thereby calculating the $IC_{50}$.

INDUSTRIAL APPLICABILITY

Since the peptide VPX of the present invention can be isolated from a casein hydrolysate, it is highly safe and can be utilized in various fields such as pharmaceuticals, foods, topical dermal formulations, functional foods, and the like.

In addition, this technology can have the following constitutions.

[1] A peptide consisting of Val-Pro-X wherein X represents an amino acid residue (except for L-proline residue).

[2] The peptide described in the aforementioned [1] wherein X is a basic amino acid residue, an aliphatic neutral amino acid residue, an amide group-carrying neutral amino acid residue, or an aromatic group-carrying neutral amino acid residue.

[3] The peptide described in the aforementioned [1] or [2] wherein X is selected from an alanine residue, a glutamine residue, a methionine residue, an asparagine residue, a glycine residue, a valine residue, a tyrosine residue, a serine residue, and a lysine residue.

[4] The peptide described any one of the aforementioned [1] to [3] wherein the peptide is one or more selected from the peptide consisting of any of the following amino acid sequences (a) to (i):

```
(a)        Val-Pro-Ala      (SEQ ID NO: 2)
(b)        Val-Pro-Gln      (SEQ ID NO: 3)
(c)        Val-Pro-Met      (SEQ ID NO: 4)
(d)        Val-Pro-Asn      (SEQ ID NO: 5)
(e)        Val-Pro-Gly      (SEQ ID NO: 6)
(f)        Val-Pro-Val
(g)        Val-Pro-Tyr      (SEQ ID NO: 8)
(h)        Val-Pro-Ser      (SEQ ID NO: 9)
(i)        Val-Pro-Lys.     (SEQ ID NO: 10)
```

Those preferred from the viewpoint of bioactivity are VPA (SEQ ID NO:2), VPQ (SEQ ID NO:3), VPN (SEQ ID NO:5), VPG (SEQ ID NO:6), VPV (SEQ ID NO:7), VPY (SEQ ID NO:8), VPS (SEQ ID NO:9), VPK (SEQ ID NO:10).

From the viewpoint of the dipeptidyl peptidase-IV inhibiting activity, VPA (SEQ ID NO:2), VPQ (SEQ ID NO:3), VPV (SEQ ID NO:7) are preferred.

From the viewpoint of the angiotensin converting enzyme inhibiting activity, VPA (SEQ ID NO:2), VPK (SEQ ID NO:10) are preferred.

[5] A dipeptidyl peptidase-IV inhibitor, a hyperglycemia ameliorating agent, a blood sugar rise suppressing agent, an anti-diabetic agent, a vascular endothelial disorder suppressing agent, a vascular ameliorating agent, an angiotensin converting enzyme inhibitor, a hypotensive agent, or an anti-hypertensive agent, which contains one or more of a peptide consisting of Val-Pro-X wherein X represents an amino acid residue (except for L-proline residue) or a peptide described in any one of the aforementioned [2] to [4] as an active ingredient.

[6] Use of a peptide consisting of Val-Pro-X wherein X represents an amino acid residue (except for L-proline residue) or the peptide described in any one of the aforementioned [2] to [4], for producing a dipeptidase-IV inhibitor, a hyperglycemia ameliorating agent, a blood sugar rise suppressing agent, an anti-diabetic agent, a vascular endothelial disorder suppressing agent, a vascular ameliorating agent, an angiotensin converting enzyme inhibitor, a hypotensive agent, or an anti-hypertensive agent.

[7] Use of a peptide consisting of Val-Pro-X wherein X represents an amino acid residue (except for L-proline residue) or a peptide described in any one of the aforementioned [2] to [4], for producing a dipeptidyl peptidase-IV-inhibiting food, a hyperglycemia ameliorating agent, a blood sugar rise-suppressing food, an anti-diabetic food, a vascular endothelial disorder-suppressing food, a vascular ameliorating food, an angiotensin converting enzyme-inhibiting food, a hypotensive treating food.

[8] Use of a peptide consisting of Val-Pro-X wherein X represents an amino acid residue (except for L-proline residue) or a peptide described in any one of the aforementioned [2] to [4], for a dipeptidyl peptidase-IV inhibitor, a hyperglycemia ameliorating agent, a blood sugar rise suppressing agent, an anti-diabetic agent, a vascular endothelial disorder suppressing agent, a vascular ameliorating agent, an angiotensin converting enzyme inhibitor, a hypotensive agent, or an anti-hypertensive agent.

[9] Use of a peptide consisting of Val-Pro-X wherein X represents an amino acid residue (except for L-proline residue) or a peptide described in any one of the aforementioned [2] to [4], for dipeptidyl peptidase-IV-inhibiting foods, hypoglycemic foods, anti-diabetic foods, vascular endothelial disorder-suppressing foods, or vascular ameliorating foods.

[10] A peptide consisting of Val-Pro-X wherein X represents an amino acid residue (except for L-proline residue) or a peptide described in any one of the aforementioned [2] to [4], for prophylaxis, improvement, or therapy of a dipeptidyl peptidase-IV-induced disease, a hyperglycemic state-induced disease, a diabetes, vascular endothelial disorder, or vascular disorder-induced disease, an angiotensin converting enzyme-induced disease, and a hypertensive state-induced disease.

[11] A method for prophylaxis, improvement, or therapy of a dipeptidyl peptidase-IV-induced disease, a hyperglycemic state-induced disease, a diabetes, vascular endothelial disorder, or vascular disorder-induced disease, an angiotensin converting enzyme-induced disease, and a hypertensive state-induced disease, administering a peptide consisting of Val-Pro-X wherein X represents an amino acid residue (except for L-proline residue) or a peptide described in any one of the aforementioned [2] to [4] as an active ingredient.

[12] A peptide consisting of Val-Pro-X wherein X represents an amino acid residue (except for L-proline residue) or a peptide described in any one of the aforementioned [2] to [4], for use in prophylaxis, improvement, or therapy of a dipeptidyl peptidase-IV-induced disease, a hyperglycemic state-induced disease, a diabetes, vascular endothelial disorder, or vascular disorder-induced disease, an angiotensin converting enzyme-induced disease, and a hypertensive state-induced disease.

[13] Use of a peptide consisting of Val-Pro-X wherein X represents an amino acid residue (except for L-proline residue) or a peptide described in any one of the aforementioned [2] to [4], for prophylaxis, improvement, or therapy of a dipeptidyl peptidase-IV-induced disease, a hyperglycemic state-induced disease, a diabetes, vascular endothelial disorder, or vascular disorder-induced disease, an angiotensin converting enzyme-induced disease, and a hypertensive state-induced disease.

[14] The dipeptidyl peptidase-IV-induced disease and/or symptoms are selected preferably from a hyperglycemic disease, diabetes, diabetes complication, a vascular endothelial disorder, and a vascular disorder.

[15] The angiotensin converting enzyme-induced disease and/or symptoms are selected preferably from hypertension and a cardiovascular disease.

[16] A peptide consisting of Val-Pro-X wherein X represents an amino acid residue (except for L-proline residue) or a peptide described in any one of the aforementioned [2] to [4] obtained by hydrolysis of a casein and a method for producing the same.

[17] A peptide consisting of Val-Pro-X wherein X represents an amino acid residue (except for L-proline residue) or a peptide described in any one of the aforementioned [2] to [4] obtained by separation and purification of a casein using the following steps:

(a) using hydrolase (preferably endopeptidase); conducting preferably under the condition at a temperature of 10 to 85° C. for 0.1 to 48 hours;

(b) using a chromatography for separation and purification of the resultant hydrolysate; preferably using one or more selected from ion exchange chromatography, reverse phase chromatography, partition chromatography, and the like;

and a method for producing the same.

Although a few embodiments of the present invention have been shown and described, it would be appreciated by those skilled in the art that changes may be made in this embodiment without departing from the principles and spirit of the invention, the scope of which is defined in the claims and their equivalents.

The invention claimed is:

1. A method of improvement or therapy of a disease selected from the group consisting of a dipeptidyl-peptidase-IV-induced disease, a hyperglycemic state-induced disease, a diabetes, vascular endothelial disorder or vascular disorder-induced disease, an angiotensin converting enzyme-induced disease, and a hypertensive state-induced disease, comprising:

administering a peptide consisting of Val-Pro-X wherein X represents an amino acid residue (except for L-proline residue and L-alanine residue) wherein X is selected from a basic amino acid residue, an aliphatic neutral amino acid residue, a hydroxyl group-carrying neutral amino acid residue, an amide group-carrying neutral amino acid residue and an aromatic group-carrying neutral amino acid residue.

2. The method according to claim 1 wherein X is selected from a glutamine residue, a methionine residue, an asparagine residue, a glycine residue, a valine residue, a tyrosine residue, a serine residue and a lysine residue.

3. The method according to claim 1, wherein the peptide is Val-Pro-Gln or Val-Pro-Val.

4. The method according to claim 1, wherein the angiotensin converting enzyme-induced disease is selected from the group consisting of hypertension, hypercardia, and renal hypertrophy.

5. The method according to claim 1, wherein the hypertensive state-induced disease is selected from the group consisting of cerebral hemorrhage, cerebral infarction, angina pectoris, myocardial infarction, renal failure, vision disorder, and angioedema.

6. The method according to claim 1, wherein the vascular endothelial disorder is diabetic vascular disorder.

7. The method according to claim 1, wherein the peptide is administered orally or parenterally.

8. The method according to claim 1, wherein the peptide is administered in a dose of 0.01 to 30 mg/day.

9. A method of improvement or therapy of a disease selected from the group consisting of a (i) dipeptidylpeptidase-IV-induced disease, except for a vascular endothelial disorder and high blood pressure, (ii) a hyperglycemic state-induced disease, and (iii) diabetes, comprising:
  administering a peptide consisting of Val-Pro-Ala, to a subject in need thereof.

\* \* \* \* \*

```
                            SEQUENCE LISTING

<160> NUMBER OF SEQ ID NOS: 34

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000
```

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16
<211> LENGTH: 4
<212> TYPE: PRT
<213> ORGANISM: Artificial sequence
<220> FEATURE:
<223> OTHER INFORMATION:
      Synthesized

<400> SEQUENCE: 16

Lys Val Leu Pro
1

<210> SEQ ID NO 17
<211> LENGTH: 8
<212> TYPE: PRT
<213> ORGANISM: Artificial sequence
<220> FEATURE:
<223> OTHER INFORMATION:
      Synthesized

<400> SEQUENCE: 17

Leu Pro Val Pro Gly Ile Asn Lys
1               5

<210> SEQ ID NO 18
<211> LENGTH: 8

```
<212> TYPE: PRT
<213> ORGANISM: Artificial sequence
<220> FEATURE:
<223> OTHER INFORMATION: Synthesized

<400> SEQUENCE: 18

Val Pro Leu Gly Thr Gly Ile Asn
1               5

<210> SEQ ID NO 19
<211> LENGTH: 7
<212> TYPE: PRT
<213> ORGANISM: Artificial sequence
<220> FEATURE:
<223> OTHER INFORMATION: Synthesized

<400> SEQUENCE: 19

Val Pro Tyr Pro Gly Ile Asn
1               5

<210> SEQ ID NO 20
<211> LENGTH: 6
<212> TYPE: PRT
<213> ORGANISM: Artificial sequence
<220> FEATURE:
<223> OTHER INFORMATION: Synthesized

<400> SEQUENCE: 20

Pro Leu Leu Gly Ile Asn
1               5

<210> SEQ ID NO 21
<211> LENGTH: 4
<212> TYPE: PRT
<213> ORGANISM: Artificial sequence
<220> FEATURE:
<223> OTHER INFORMATION: Synthesized

<400> SEQUENCE: 21

Gly Pro Phe Pro
1

<210> SEQ ID NO 22
<211> LENGTH: 7
<212> TYPE: PRT
<213> ORGANISM: Artificial sequence
<220> FEATURE:
<223> OTHER INFORMATION: Synthesized

<400> SEQUENCE: 22

Leu Pro Val Pro Gly Ile Asn
1               5

<210> SEQ ID NO 23
<211> LENGTH: 7
<212> TYPE: PRT
<213> ORGANISM: Artificial sequence
<220> FEATURE:
<223> OTHER INFORMATION: Synthesized

<400> SEQUENCE: 23

Leu Pro Gly Ile Asn Tyr Leu
1               5

<210> SEQ ID NO 24
<211> LENGTH: 4
<212> TYPE: PRT
```

```
<213> ORGANISM: Artificial sequence
<220> FEATURE:
<223> OTHER INFORMATION: Synthesized

<400> SEQUENCE: 24

Met Pro Leu Trp
1

<210> SEQ ID NO 25
<211> LENGTH: 6
<212> TYPE: PRT
<213> ORGANISM: Artificial sequence
<220> FEATURE:
<223> OTHER INFORMATION: Synthesized

<400> SEQUENCE: 25

Tyr Val Pro Glu Pro Phe
1               5

<210> SEQ ID NO 26
<211> LENGTH: 6
<212> TYPE: PRT
<213> ORGANISM: Artificial sequence
<220> FEATURE:
<223> OTHER INFORMATION: Synthesized

<400> SEQUENCE: 26

Pro Gln Ser Val Leu Ser
1               5

<210> SEQ ID NO 27

<400> SEQUENCE: 27

000

<210> SEQ ID NO 28
<211> LENGTH: 4
<212> TYPE: PRT
<213> ORGANISM: Artificial sequence
<220> FEATURE:
<223> OTHER INFORMATION: Synthesized

<400> SEQUENCE: 28

Leu Pro Val Pro
1

<210> SEQ ID NO 29
<211> LENGTH: 6
<212> TYPE: PRT
<213> ORGANISM: Artificial sequence
<220> FEATURE:
<223> OTHER INFORMATION: Synthesized

<400> SEQUENCE: 29

Glu Met Pro Phe Pro Lys
1               5

<210> SEQ ID NO 30
<211> LENGTH: 4
<212> TYPE: PRT
<213> ORGANISM: Artificial sequence
<220> FEATURE:
<223> OTHER INFORMATION: Synthesized

<400> SEQUENCE: 30

Leu Pro Leu Pro
```

```
-continued

<210> SEQ ID NO 31
<211> LENGTH: 7
<212> TYPE: PRT
<213> ORGANISM: Artificial sequence
<220> FEATURE:
<223> OTHER INFORMATION:
      Synthesized

<400> SEQUENCE: 31

Gly Pro Phe Pro Ile Ile Val
1               5

<210> SEQ ID NO 32
<211> LENGTH: 7
<212> TYPE: PRT
<213> ORGANISM: Artificial sequence
<220> FEATURE:
<223> OTHER INFORMATION: Synthesized

<400> SEQUENCE: 32

Gly Pro Phe Pro Ile Ile Val
1               5

<210> SEQ ID NO 33
<211> LENGTH: 6
<212> TYPE: PRT
<213> ORGANISM: Artificial sequence
<220> FEATURE:
<223> OTHER INFORMATION: Synthesized

<400> SEQUENCE: 33

His Pro Leu Ile Glu Lys
1               5

<210> SEQ ID NO 34
<211> LENGTH: 7
<212> TYPE: PRT
<213> ORGANISM: Artificial sequence
<220> FEATURE:
<223> OTHER INFORMATION: Synthesized

<400> SEQUENCE: 34

Ala Pro Phe Pro Glu Val Phe
1               5
```